United States Patent
Bhagat et al.

(10) Patent No.: US 10,463,422 B2
(45) Date of Patent: Nov. 5, 2019

(54) SURGICAL INSTRUMENT WITH STOPPER ASSEMBLY

(71) Applicant: COVIDIEN LP, Mansfield, MA (US)

(72) Inventors: Simranjeet Bhagat, Punjab (IN); Victor Appel, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 359 days.

(21) Appl. No.: 14/574,693

(22) Filed: Dec. 18, 2014

(65) Prior Publication Data

US 2016/0175026 A1 Jun. 23, 2016

(51) Int. Cl.
| | | |
|---|---|---|
| *A61B 18/14* | (2006.01) | |
| *A61B 17/29* | (2006.01) | |
| *A61B 18/00* | (2006.01) | |
| *A61B 17/295* | (2006.01) | |
| *A61B 90/00* | (2016.01) | |
| *A61B 17/00* | (2006.01) | |

(52) U.S. Cl.
CPC .......... *A61B 18/1445* (2013.01); *A61B 17/29* (2013.01); *A61B 17/295* (2013.01); *A61B 2017/0046* (2013.01); *A61B 2017/2903* (2013.01); *A61B 2017/2946* (2013.01); *A61B 2018/00297* (2013.01); *A61B 2018/1455* (2013.01); *A61B 2090/034* (2016.02)

(58) Field of Classification Search
CPC .............................................. A61B 2017/2903
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |

(Continued)

FOREIGN PATENT DOCUMENTS

| | | |
|---|---|---|
| CN | 201299462 | 9/2009 |
| DE | 2415263 A1 | 10/1975 |

(Continued)

OTHER PUBLICATIONS

Your Dictionary, "with", WayBackMachine, Aug. 15, 2014, <https://web.archive.org/web/20140815124722/http://www.yourdictionary.com/with>.*

(Continued)

*Primary Examiner* — Linda C Dvorak
*Assistant Examiner* — Ryan T Clark

(57) ABSTRACT

A surgical instrument includes a housing, an elongated member that extends distally from the housing and defines a longitudinal axis, an end effector assembly coupled to a distal portion of the elongated member, and a stopper assembly operably coupled to the proximal portion of the outer shaft member. The stopper assembly is disposed within one or more cavities defined within the housing. The stopper assembly is configured to prevent longitudinal movement of the outer shaft member along the longitudinal axis and to rotate within the one or more cavities upon rotation of the elongated member about the longitudinal axis.

8 Claims, 8 Drawing Sheets

(56) References Cited

U.S. PATENT DOCUMENTS

| | | |
|---|---|---|
| D349,341 S | 8/1994 | Lichtman et al. |
| D354,564 S | 1/1995 | Medema |
| 5,382,255 A | 1/1995 | Castro et al. |
| D358,887 S | 5/1995 | Feinberg |
| D384,413 S | 9/1997 | Zlock et al. |
| H1745 H | 4/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| D680,220 S | 4/2013 | Rachlin |
| 2003/0181910 A1* | 9/2003 | Dycus ............... A61B 18/1445 606/51 |
| 2010/0030218 A1* | 2/2010 | Prevost ............. A61B 17/1655 606/80 |
| 2011/0077649 A1* | 3/2011 | Kingsley ........... A61B 18/1445 606/52 |
| 2012/0078244 A1* | 3/2012 | Worrell ........... A61B 17/07207 606/33 |
| 2012/0245432 A1* | 9/2012 | Karpowicz ....... A61B 17/0206 600/224 |
| 2012/0296371 A1* | 11/2012 | Kappus ............. A61B 17/295 606/205 |
| 2013/0023729 A1* | 1/2013 | Vazales ............. A61B 1/0669 600/104 |
| 2014/0025071 A1* | 1/2014 | Sims ................ A61B 18/1445 606/46 |
| 2014/0221994 A1 | 8/2014 | Reschke |
| 2014/0221995 A1 | 8/2014 | Guerra et al. |
| 2014/0221999 A1 | 8/2014 | Cunningham et al. |
| 2014/0228842 A1 | 8/2014 | Dycus et al. |
| 2014/0230243 A1 | 8/2014 | Roy et al. |
| 2014/0236149 A1 | 8/2014 | Kharin et al. |
| 2014/0243811 A1 | 8/2014 | Reschke et al. |
| 2014/0243824 A1 | 8/2014 | Gilbert |
| 2014/0249528 A1 | 9/2014 | Hixson et al. |
| 2014/0250686 A1 | 9/2014 | Hempstead et al. |
| 2014/0257274 A1 | 9/2014 | McCullough, Jr. et al. |
| 2014/0257283 A1 | 9/2014 | Johnson et al. |
| 2014/0257284 A1 | 9/2014 | Artale |
| 2014/0257285 A1* | 9/2014 | Moua ................ A61B 17/282 606/52 |
| 2014/0276803 A1 | 9/2014 | Hart |
| 2014/0284313 A1 | 9/2014 | Allen, IV et al. |
| 2014/0284841 A1 | 9/2014 | Ackley et al. |
| 2014/0288549 A1 | 9/2014 | McKenna et al. |
| 2014/0288553 A1 | 9/2014 | Johnson et al. |
| 2014/0288557 A1 | 9/2014 | Larson et al. |
| 2014/0330298 A1* | 11/2014 | Arshonsky ..... A61B 17/320092 606/169 |
| 2014/0330308 A1 | 11/2014 | Hart et al. |
| 2014/0336635 A1 | 11/2014 | Hart et al. |
| 2014/0353188 A1 | 12/2014 | Reschke et al. |
| 2015/0018816 A1 | 1/2015 | Latimer |
| 2015/0025528 A1 | 1/2015 | Arts |
| 2015/0032106 A1 | 1/2015 | Rachlin |
| 2015/0082922 A1* | 3/2015 | Joseph .............. A61B 17/29 74/54 |
| 2016/0100882 A1* | 4/2016 | Boudreaux ....... A61B 18/1445 606/52 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| EP | 1301135 B1 * | 9/2005 | ........ A61B 18/1445 |
| EP | 2659848 A2 * | 11/2013 | ........ A61B 18/1445 |
| EP | 2692297 A2 | 2/2014 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |

(56) References Cited

FOREIGN PATENT DOCUMENTS

| | | |
|---|---|---|
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/07627 | 1/2002 |
| WO | 02/045589 | 6/2002 |
| WO | 06/021269 A1 | 3/2006 |
| WO | 05110264 A3 | 4/2006 |
| WO | 08/040483 A1 | 4/2008 |
| WO | 2011/018154 A1 | 2/2011 |

OTHER PUBLICATIONS

U.S. Appl. No. 14/253,017, filed Apr. 15, 2014; inventor: Orszulak.
U.S. Appl. No. 14/260,905, filed Apr. 24, 2014; inventor: Jensen.
U.S. Appl. No. 14/268,051, filed May 2, 2014; inventor: Hart.
U.S. Appl. No. 14/268,140, filed May 2, 2014; inventor: Twomey.
U.S. Appl. No. 14/276,465, filed May 13, 2014; inventor: Kappus.
U.S. Appl. No. 14/295,049, filed Jun. 3, 2014; inventor: Couture.
U.S. Appl. No. 14/295,730, filed Jun. 4, 2014; inventor: Sartor.
U.S. Appl. No. 14/319,869, filed Jun. 30, 2014; inventor: Cunningham.
U.S. Appl. No. 14/322,513, filed Jul. 2, 2014; inventor: Duffin.
U.S. Appl. No. 14/335,303, filed Jul. 18, 2014; inventor: Lee.
Partial European Search Report corresponding to counterpart Int'l Appln. No. EP 15 19 1736.6, dated Jun. 6, 2016.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

(56) References Cited

OTHER PUBLICATIONS

Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed Dec. 17, 2008; inventor: Paul R. Sremeich.
U.S. Appl. No. 13/731,674, filed Dec. 31, 2012; inventor: Siebrecht.
EP Search Report corresponding to counterpart Int'l Appln. No. EP 15 19 1736.6 completed Oct. 27, 2016.
European Examination Report issued in Appl. No. EP 15 191 736.6 dated Apr. 26, 2018 (6 pages).

* cited by examiner

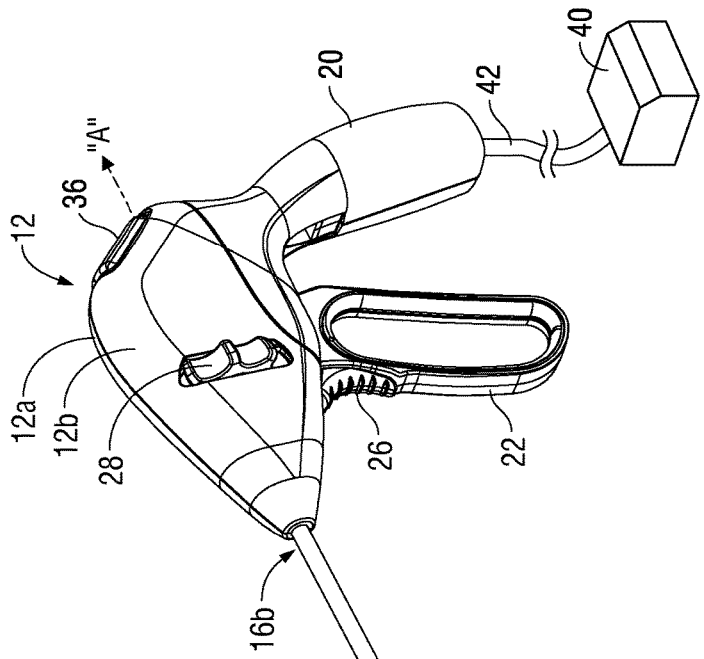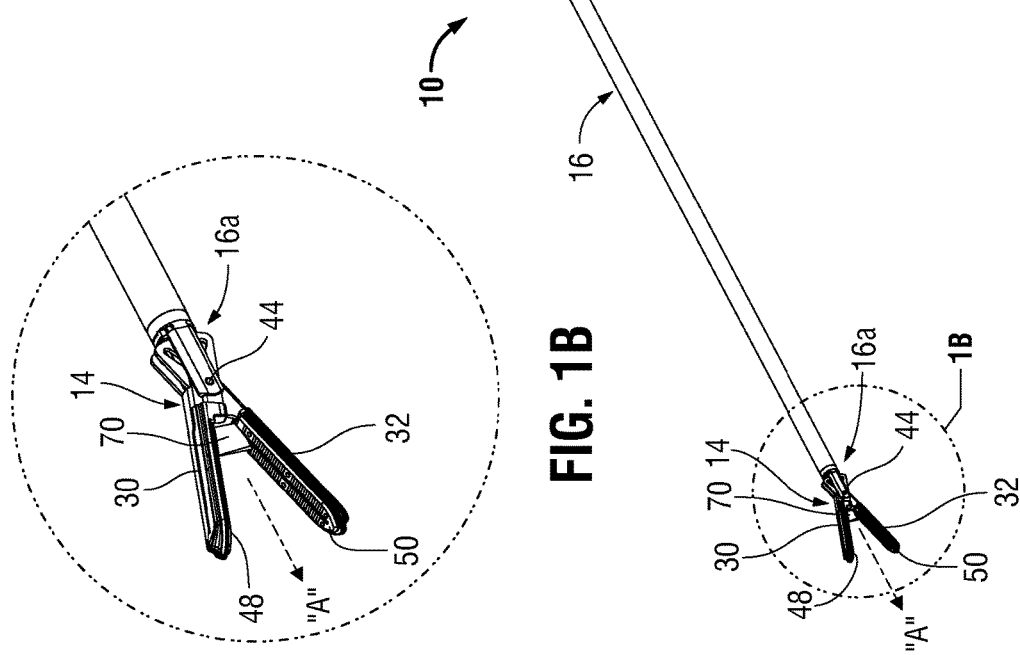

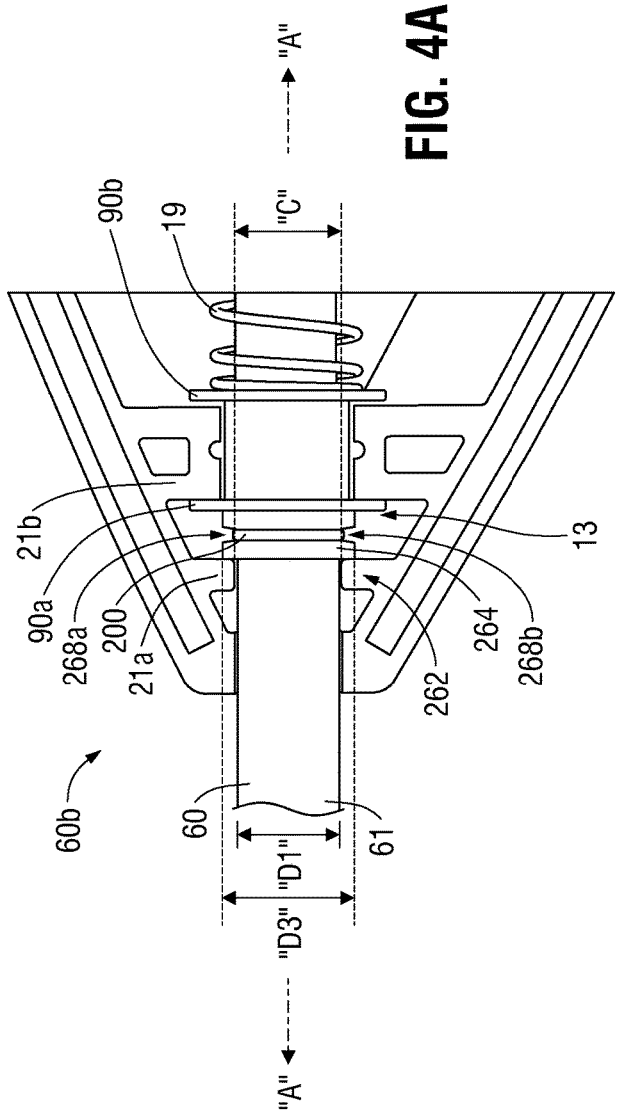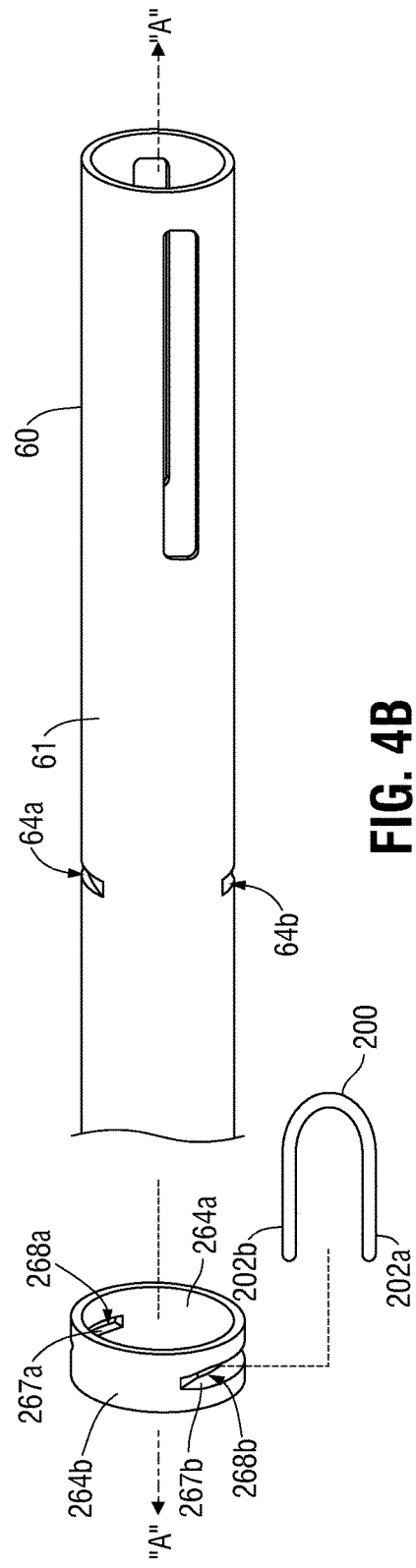

SURGICAL INSTRUMENT WITH STOPPER ASSEMBLY

BACKGROUND

1. Technical Field

The present disclosure relates generally to the field of surgical instruments. In particular, the disclosure relates to an endoscopic electrosurgical forceps having a housing including a mechanism disposed therein that prevents longitudinal movement of an elongated member extending from the housing.

2. Background of Related Art

Electrosurgical forceps are commonly used in open and endoscopic surgical procedures to coagulate, cauterize and seal tissue. Such forceps typically include a housing and a pair of jaws disposed on a distal portion of an elongated member extending from the housing. The pair of jaws can be controlled by a surgeon to grasp targeted tissue, such as, e.g., a blood vessel. The jaws may be approximated to apply a mechanical clamping force to the tissue, and are associated with at least one electrode to permit the delivery of electrosurgical energy to the tissue. The combination of the mechanical clamping force and the electrosurgical energy has been demonstrated to join adjacent layers of tissue captured between the jaws. When the adjacent layers of tissue include the walls of a blood vessel, sealing the tissue may result in hemostasis, which may facilitate the transection of the sealed tissue. A detailed discussion of the use of an electrosurgical forceps may be found in U.S. Pat. No. 7,255,697 to Dycus et al.

Operation of the electrosurgical forceps typically involves longitudinal actuation of the internal components of the elongated member as well as rotational actuation of the elongated member. During use, longitudinal actuation of such internal components may result in inadvertent longitudinal movement of the elongated member relative to the housing. Thus, the elongated member must be prevented from longitudinal movement while its rotational actuation functionality is maintained.

SUMMARY

The present disclosure relates to a surgical instrument that includes a housing, an elongated member that extends distally from the housing and defines a longitudinal axis, an end effector assembly coupled to a distal portion of the elongated member, and a stopper assembly operably coupled to the proximal portion of the outer shaft member. The elongated member is configured to rotate about the longitudinal axis and includes an outer shaft member having a proximal portion disposed within the housing. The end effector assembly includes a pair of opposing jaw members moveable relative to each other to grasp tissue therebetween. At least one of the jaw members is adapted to connect to an electrosurgical energy source for conducting electrosurgical energy through grasped tissue. The stopper assembly is disposed within at least one cavity defined within the housing. The stopper assembly is configured to prevent longitudinal movement of the outer shaft member along the longitudinal axis and to rotate within the at least one cavity upon rotation of the elongated member about the longitudinal axis.

Additionally or alternatively, the stopper assembly includes at least one annular member coupled to an outer surface of the outer shaft member and includes at least one slot defined through the annular member perpendicular to the longitudinal axis.

Additionally or alternatively, the outer shaft member defines at least one groove therein perpendicular to the longitudinal axis, the at least one groove configured to align with the at least one slot of the at least one annular member.

Additionally or alternatively, the at least one groove of the outer shaft member and the at least one slot of the annular member are configured to receive a clip therein to couple the at least one annular member to the outer shaft member.

Additionally or alternatively, the diameter of the outer shaft member is less than a diameter of the at least one annular member.

Additionally or alternatively, the at least one cavity is defined by a distal wall and a proximal wall each defining an annular clearance configured to receive the outer shaft member therethrough.

Additionally or alternatively, the diameter of the at least one annular member is greater than a diameter of the annular clearance of at least one of the distal wall or the proximal wall such that the at least one annular member engages at least one of the distal wall or the proximal wall.

Additionally or alternatively, at least one annular member includes an inner surface defining at least one rib configured to engage a longitudinal slot defined through the proximal portion of the outer shaft member.

Additionally or alternatively, the stopper assembly includes a first annular member and a second annular member, the first annular member restricting proximal longitudinal movement of the outer shaft member along the longitudinal axis and the second annular member restricting distal longitudinal movement of the outer shaft member along the longitudinal axis.

Additionally or alternatively, the stopper assembly includes at least one surface structure protruding from an outer surface of the outer shaft member, the at least one surface structure configured to engage at least one wall defining the at least one cavity.

Additionally or alternatively, the stopper assembly includes a key member disposed within a key slot extending through the proximal portion of the outer shaft member, at least a portion of the key member protruding from the outer shaft member and configured to engage at least one wall defining the at least one cavity.

In another aspect, the present disclosure relates to a surgical instrument that includes a housing having at least one cavity defined therein, an elongated member that extends distally from the housing and defines a longitudinal axis, an end effector assembly coupled to a distal portion of the elongated member, and a stopper assembly operably coupled to the proximal portion of the outer shaft member. The elongated member is configured to rotate about the longitudinal axis and includes an outer shaft member having a proximal portion disposed within the at least one cavity. The end effector assembly includes a pair of opposing jaw members moveable relative to each other to grasp tissue therebetween. At least one of the jaw members is adapted to connect to an electrosurgical energy source for conducting electrosurgical energy through grasped tissue. The stopper assembly is rotatable within the at least one cavity upon rotation of the elongated member and about the longitudinal axis. The stopper assembly is configured to engage at least one wall defining the at least one cavity to prevent longitudinal movement of the outer shaft member along the longitudinal axis.

Additionally or alternatively, the stopper assembly includes at least one lance protruding from the outer shaft member.

In another aspect, the present disclosure relates to a surgical instrument that includes a housing at least one cavity defined therein, an elongated member that extends distally from the housing and defines a longitudinal axis, an end effector assembly coupled to a distal portion of the elongated member, and a stopper assembly operably coupled to the proximal portion of the outer shaft member. The at least one cavity in the housing is defined by a distal wall and a proximal wall each defining an annular clearance. The elongated member is configured to rotate about the longitudinal axis and includes an outer shaft member having a proximal portion disposed within the annular clearance of the distal and proximal walls. The end effector assembly includes a pair of opposing jaw members moveable relative to each other to grasp tissue therebetween. At least one of the jaw members is adapted to connect to an electrosurgical energy source for conducting electrosurgical energy through grasped tissue. The stopper assembly is rotatable within the at least one cavity upon rotation of the elongated member about the longitudinal axis. The stopper assembly includes a diameter that is greater than a diameter of at least one of the annular clearances defined by one of the distal wall or the proximal wall such that the stopper assembly is configured to engage at least one of the distal wall or the proximal wall to prevent longitudinal movement of the outer shaft member along the longitudinal axis.

Additionally or alternatively, the stopper assembly is configured to be welded to the outer shaft member.

Additionally or alternatively, the stopper assembly includes at least one surface structure protruding from an outer surface of the outer shaft member and configured to engage the distal wall to prevent longitudinal movement of the outer shaft member along the longitudinal axis.

According to another aspect of the present disclosure, the stopper assembly includes a key member disposed within a key slot extending through the proximal portion of the outer shaft member, at least a portion of the key member protruding from the outer shaft member and configured to engage the distal wall to prevent longitudinal movement of the outer shaft member along the longitudinal axis.

Additionally or alternatively, a diameter of the outer shaft member is less than a diameter of the at least one annular member.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 1A is a perspective view of an electrosurgical forceps according to an embodiment of the present disclosure including a housing, an elongated member, and an end effector assembly;

FIG. 1B is an enlarged perspective view of the end effector assembly of FIG. 1A;

FIG. 4A is an enlarged side view of an embodiment of the stopper assembly of FIG. 2 including an annular member clipped to the outer shaft member;

FIG. 4B is a perspective view of the outer shaft member and the stopper assembly of FIG. 4A with parts separated;

DETAILED DESCRIPTION

Figure 2:
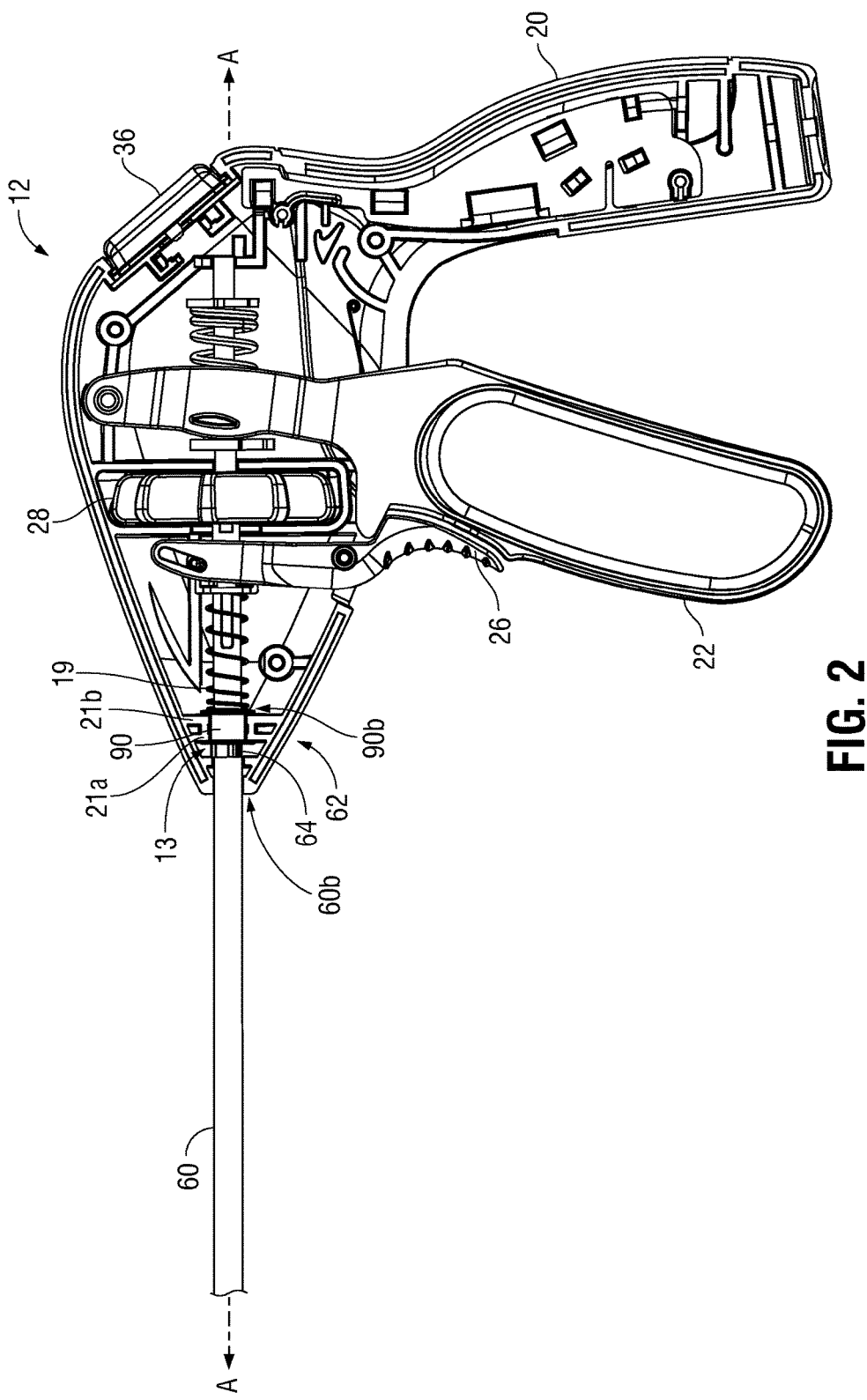
FIG. 2 is a partial, side view of a proximal portion of the electrosurgical forceps of FIG. 1 including a housing having a stopper assembly disposed therein.

Embodiments of the presently disclosed surgical system, instruments, and methods will now be described in detail with reference to the drawings, in which like reference numerals designate identical or corresponding elements in each of the several views. As used herein, the term "distal" refers to that portion of the surgical instrument or components thereof, farther from the user, while the term "proximal" refers to that portion of the surgical or components thereof, closer to the user.

The present disclosure generally provides for a surgical instrument having an end effector assembly, an elongated member defining a longitudinal axis, and a housing. The elongated member includes an outer shaft member having a proximal portion secured within the housing. A stopper assembly is disposed on the proximal portion of the outer shaft member and prevents longitudinal movement of the outer shaft member with respect to the housing while allowing the elongated member, including the outer shaft member, to freely rotate about the longitudinal axis defined by the elongated member.

In some embodiments, the stopper assembly includes one or more annular members fixed to the outer shaft member and disposed within a cavity defined within the housing. In some embodiments, the stopper assembly includes surface structures (e.g., protrusions, recesses, grooves, slots) formed on the outer shaft member using a machining process.

In some embodiments, the stopper assembly includes a key member disposed within a key slot defined through the outer shaft member such that the key member is disposed within a cavity defined within the housing.

Referring initially to FIGS. 1 and 2, an embodiment of an electrosurgical forceps 10 generally includes a housing 12 coupled to a proximal portion 16b of an elongated member 16. The housing 12 supports various actuators for remotely controlling an end effector assembly 14 coupled to a distal portion 16a of the elongated member 16. The end effector assembly 14 includes a pair of opposing jaw members 30, 32 mechanically coupled to the elongated member 16 about a pivot 44. Although this configuration is typically associated with instruments for use in laparoscopic or endoscopic surgical procedures, various aspects of the present disclosure may be practiced with traditional open instruments and in connection with endoluminal procedures as well.

The housing 12 is constructed of a right housing half 12a and a left housing half 12b. The left and right designation of the housing halves 12a, 12b refer to the respective directions as perceived by an operator using the forceps 10. The housing halves 12a, 12b may be constructed of sturdy plastic, and may be joined to one another by adhesives, ultrasonic welding or other suitable assembly methods.

To mechanically control the end effector assembly 14, the housing 12 supports a stationary handle 20, a movable handle 22, and a rotation knob 28. The movable handle 22 is movable relative to the stationary handle 20 to move the end effector assembly 14 between an open configuration (FIGS. 1A and 1B) wherein the jaw members 30, 32 are disposed in spaced relation relative to one another, and a closed configuration (not shown) wherein the jaw members 30, 32 are approximated.

A trigger 26 is supported by the housing 12 and is operable to extend and retract a knife 70 (FIGS. 1A and 1B) through the end effector assembly 14 when the end effector assembly 14 is in the closed configuration. The rotation knob 28 serves to rotate the elongated member 16 and the end effector assembly 14 about a longitudinal axis "A-A" defined by the elongated member 16.

To electrically control the end effector assembly 14, the housing 12 supports a switch 36 thereon, which is operable by the user to initiate and terminate the delivery of electrosurgical energy to the end effector assembly 14. The switch 36 is in electrical communication with an electrosurgical energy source, such as, for example, a generator 40 (see FIG. 1) or a battery (not shown) supported within the housing 12. The generator 40 may include devices such as the LIGA-SURE® Vessel Sealing Generator and the Force Triad® Generator as sold by Covidien LP. A cable 42 extends from the housing 12 to the generator 40 to electrically couple the end effector assembly 14 to the generator 40. More specifically, the jaw members 30, 32 are electrically coupled to the generator 40 (e.g., via suitable wiring extending through the elongated member 16 and the housing 12) to provide an electrical pathway to a pair of electrically conductive, tissue sealing surfaces 48, 50 disposed on the jaw members 30, 32, respectively. Sealing surfaces 48 and 50 may be electrically coupled to terminals of opposite polarity, e.g., positive (+) and negative (−), associated with the generator 40 to deliver bipolar energy to tissue grasped between jaw members 30, 32. Alternatively, the sealing surfaces 48 and 50 may be configured to deliver monopolar energy to tissue. In a monopolar configuration, one or both sealing plates 48 and 50 deliver electrosurgical energy from a positive (+) terminal and a return pad (not shown) is placed on a patient to provide a return path to the negative (−) terminal.

Electrosurgical energy may be delivered to tissue clasped between the jaw members 30, 32 through the sealing surfaces 48, 50 to effect a tissue seal. Once a tissue seal is established, the knife 70 may be advanced distally to transect the sealed tissue. The knife 70 is depicted in FIGS. 1A and 1B as extending from the elongated member 16 while the end effector assembly 14 is in an open configuration. In some embodiments, a mechanism (not shown) may be provided to prevent advancement of the knife 70 through the jaw members 30, 32 when the end effector assembly 14 is in the open configuration.

The elongated member 16 includes various longitudinal components that operatively couple the end effector assembly 14 to the various actuators supported by the housing 12. Referring now to FIG. 2, an outer shaft member 60 defines an exterior surface of the elongated member 16 and supports movement of other components therethrough as described below. A spindle 90 is disposed within the housing 12 and serves to secure at least a portion of the outer shaft member 60 within the housing 12. The spindle 90 includes an annular throughbore (not shown) defined therethrough, through which the proximal portion 60b of the outer shaft member 60 extends, thereby ensuring proper alignment of the elongated member 16 relative to the housing 12. In some embodiments, the outer shaft member 60 may rotate about the longitudinal axis "A-A" relative to the spindle 90. In other embodiments, outer shaft member 60 may be fixedly coupled to spindle 90 such that rotation of outer shaft member 60 about the longitudinal axis "A-A" translates corresponding rotation of spindle 90. A spring 19 is disposed about the outer shaft member 60 within housing 12 and is caused to compress against a proximal surface 90b of spindle 90 when trigger 26 is actuated (not shown) to induce advancement of the knife 70 along the longitudinal axis "A-A" and through the jaw members 30, 32. Specifics of the operation of the trigger 26 to induce advancement of the knife 70 through the jaw members 30, 32 is described in U.S. Patent Application Publication No. 20130296922, the entire contents of which is incorporated herein by reference.

Figure 3A:
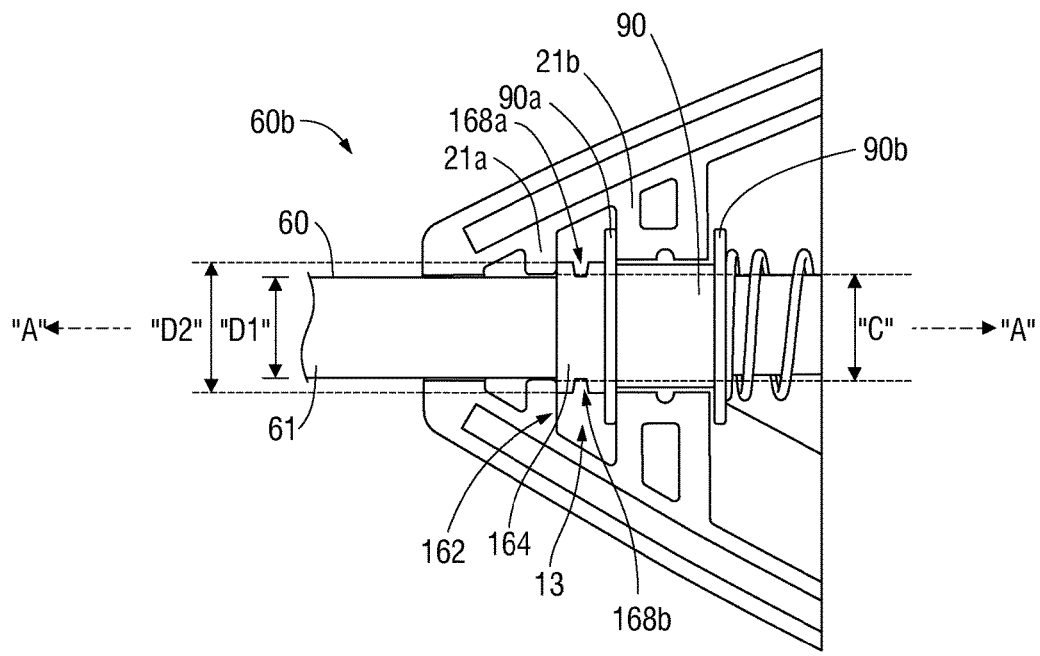
FIG. 3A is an enlarged side view of an embodiment of the stopper assembly of FIG. 2 including an annular member coupled to an outer shaft member of the elongated member.

A stopper assembly 62 coupled to the proximal portion 60b of the outer shaft member 60 is disposed within a cavity 13 defined within housing 12 between a distal interior wall 21a and a proximal interior wall 21b (see, e.g., FIG. 3A). As described below with reference to the various embodiments shown in FIGS. 3A-7C, the stopper assembly 62 serves to prevent longitudinal movement of the outer shaft member 60 along the longitudinal axis "A-A".

Figure 3B:
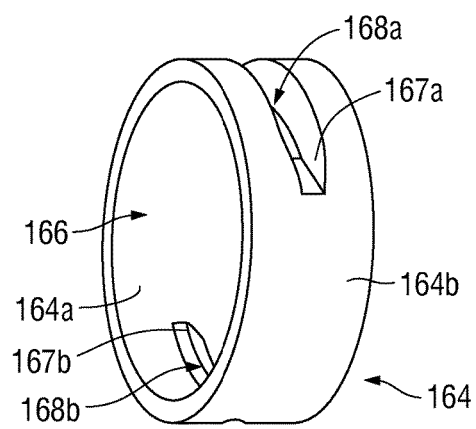
FIG. 3B is an enlarged perspective view of the annular member of FIG. 3A.

Referring now to FIGS. 3A and 3B, one embodiment of a stopper assembly 162 is shown and includes an annular member 164 disposed on the proximal portion 60b of the outer shaft member 60. Annular member 164 includes a diameter "D2" that is larger than a diameter "D1" of the outer shaft member 60. An inner surface 164a of the annular member 164 defines a through hole 166 configured to receive outer shaft member 60 therethrough such that an outer surface 61 of outer shaft member 60 engages the inner surface 164a of annular member 164. Annular member 164 may be fixed to outer shaft member 60 using various suitable methods such as, for example, friction fit, adhesives, and welding. Annular member 164 defines a pair of opposing slots 168a, 168b therethrough perpendicular to longitudinal axis "A-A" and extending between outer surface 164b and inner surface 164a to define a pair of corresponding inner surfaces 167a, 167b. Welding materials or adhesive may be applied to the inner surfaces 167a, 167b to couple annular member 164 to the outer surface 61 of the outer shaft member 60. While annular member 164 is shown in FIG. 3B to include a pair of slots 168a, 168b, in some embodiments annular member 164 may include a single slot or, alternatively, three or more slots. In some embodiments, annular member 164 may be welded to outer shaft member 60 through slots 168a, 168b, via welding, laser welding, or any other suitable welding method. An advantage of welding the annular member 164 to outer shaft member 60 through the slots 168a, 168b is that welding materials used in the welding process (e.g., metal, thermoplastic, etc.) remain within slots 168a, 168b instead of on the outer surface 164b of annular member 164 or around the outer perimeter of the annular member 164.

Annular member 164 is free to rotate within cavity 13 upon rotation of elongated member 16 about longitudinal axis "A-A" and is prevented from distal longitudinal movement by engagement with distal wall 21a and proximal longitudinal movement by a distal surface 90a of spindle 90. Spindle 90, in turn, is prevented from proximal longitudinal movement by engagement of distal surface 90a with proximal wall 21b. Distal wall 21a defines an annular clearance "C" through which outer shaft member 60 longitudinally extends. Since annular member 164 is fixedly coupled to outer shaft member 60 and the diameter "D2" of annular member 164 is greater than the diameter of annular clearance "C", distal longitudinal movement of outer shaft member 60 along longitudinal axis "A-A" is prevented. Due to the engagement of annular member 164 with the distal surface 90a of spindle 90, proximal longitudinal movement of outer shaft member 60 along longitudinal axis "A-A" is prevented.

Referring now to FIGS. 4A and 4B, another embodiment of a stopper assembly 262 is shown and includes an annular member 264 disposed around the proximal portion 60b of the outer shaft member 60. Annular member 264 defines a pair of opposing slots 268a, 268b therethrough perpendicular to longitudinal axis "A-A" and extending between an outer surface 264b and an inner surface 264a of annular member 264. Slots 268a, 268b are configured to receive free-ends 202a, 202b of a generally U-shaped clip member 200. In this embodiment, the proximal portion 60b of outer shaft member 60 includes a pair of opposing grooves 64a, 64b formed circumferentially within a portion of outer surface 61. Outer shaft member 60 is disposed through annular member 264 such that slots 268a, 268b of annular member 264 are disposed in general alignment with grooves 64a, 64b of outer shaft member 60. Thus, free-ends 202a, 202b may be received within slots 268a, 268b and grooves 64a, 64b. Free-ends 202a, 202b are biased inwardly toward each other to aid in maintaining the clip member 200 within slots 268a, 268b and grooves 64a, 64b.

As substantially described above with respect to annular member 164 shown in FIGS. 3A and 3B, annular member 264 is disposed within and is free to rotate within cavity 13 upon rotation of elongated member 16 about longitudinal axis "A-A". Since annular member 264 is coupled to outer shaft member 60 and a diameter "D3" of annular member 264 is greater than the diameter of annular clearance "C", distal longitudinal movement of outer shaft member 60 along longitudinal axis "A-A" is prevented. Due to the engagement of annular member 264 with the distal surface 90a of spindle 90, proximal longitudinal movement of outer shaft member 60 along longitudinal axis "A-A" is prevented.

Figure 5A:
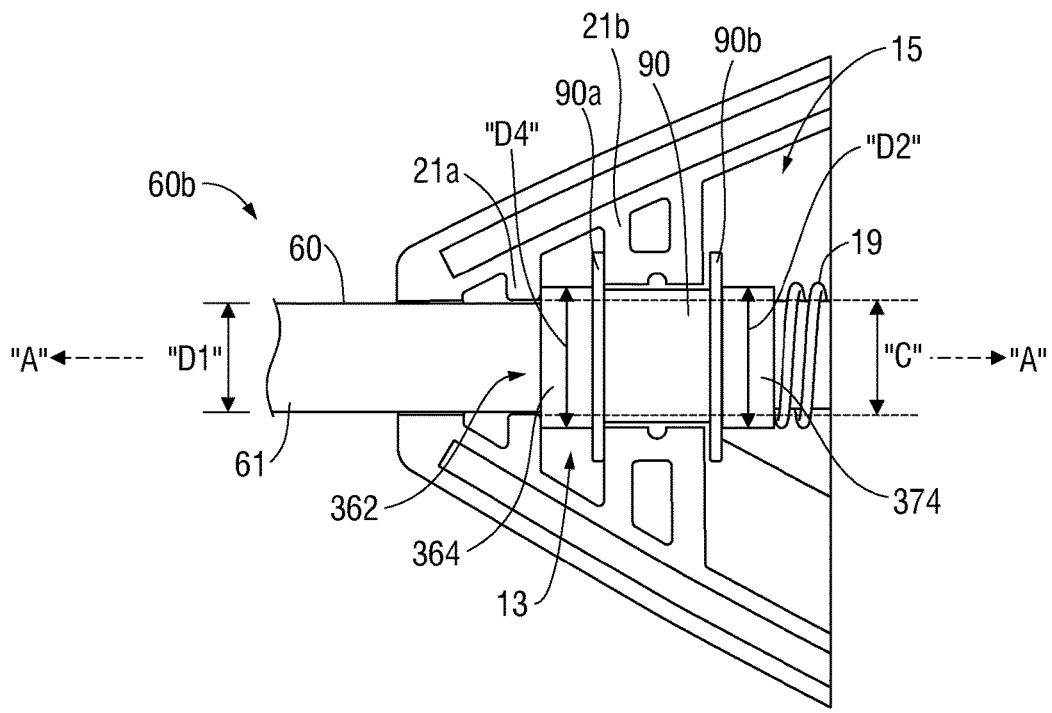
FIG. 5A is an enlarged side view of an embodiment of the stopper assembly of FIG. 2 including two annular members removably fixed to the outer shaft member.
Figure 5B:
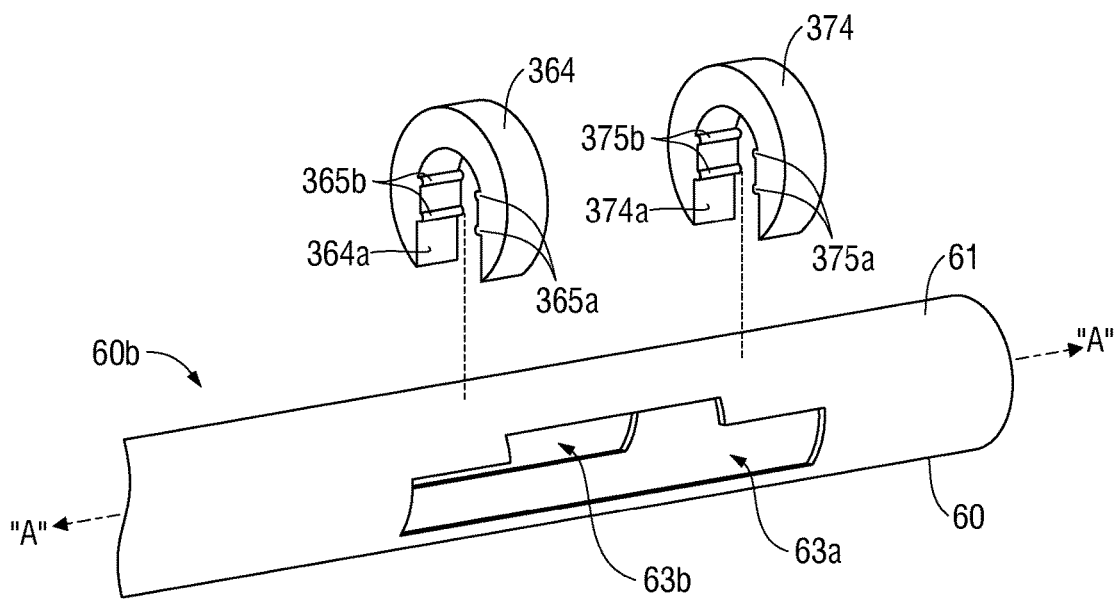
FIG. 5B is a perspective view of the outer shaft member and the stopper assembly of FIG. 5A with parts separated.

Referring now to FIGS. 5A and 5B, another embodiment of a stopper assembly 362 is shown and includes a distal annular member 364 disposed within cavity 13 and a proximal annular member 374 disposed within a cavity 15 defined within housing 12 proximal to cavity 13. Proximal and distal annular members 364, 374 each include a diameter "D4" that is larger than the diameter "D1" of outer shaft member 60. Distal annular member 364 prevents distal and proximal longitudinal movement of outer shaft member 60 and proximal annular member 374 prevents distal longitudinal movement of outer shaft member 60. Distal annular member 364 includes an inner surface 364a defining two pairs of opposing ribs 365a, 365b configured to engage a distal portion of longitudinal slots 63a, 63b, respectively, in a friction-fit manner. Likewise, proximal annular member 374 includes an inner surface 374a defining two pairs of opposing ribs 375a, 375b configured to engage a proximal portion of slots 63a, 63b, respectively, in a friction-fit manner.

With reference to FIG. 5B, each of longitudinal slots 63a, 63b include a widened middle portion (only viewable with respect to longitudinal slot 63a) to aid in coupling and decoupling of distal and proximal annular members 364, 374 with outer shaft member 60. Specifically, distal and proximal annular members 364, 374 may be coupled to outer shaft member 60 by inserting the pairs of ribs 365a, 365 and 374a, 374b into corresponding longitudinal slots 63a, 63b at the widened middle portion. Distal annular member 364 may then be translated distally such that the pairs of ribs 365a, 365b friction-fit into the distal portion of the respective longitudinal slots 63a, 63b. Similarly, proximal annular member 374 may then be translated proximally such that the pairs of ribs 375a, 375b friction-fit into the proximal portion of the respective longitudinal slots 63a, 63b.

As substantially described above with respect to annular member 164 shown in FIGS. 3A and 3B, distal annular member 364 is disposed within and is free to rotate within cavity 13 upon rotation of elongated member 16 about longitudinal axis "A-A". As referring to FIG. 5A, since distal annular member 364 is coupled to outer shaft member 60 and diameter "D4" of distal annular member 364 is greater than the annular clearance "C", distal longitudinal movement of outer shaft member 60 along longitudinal axis "A-A" is prevented. Due to the engagement of distal annular member 364 with the distal surface 90a of spindle 90, proximal longitudinal movement of outer shaft member 60 along longitudinal axis "A-A" is prevented. Distal longitudinal movement of outer shaft member 60 is also prevented due to the engagement of proximal annular member 374 with proximal surface 90b of spindle 90.

Figure 6A:
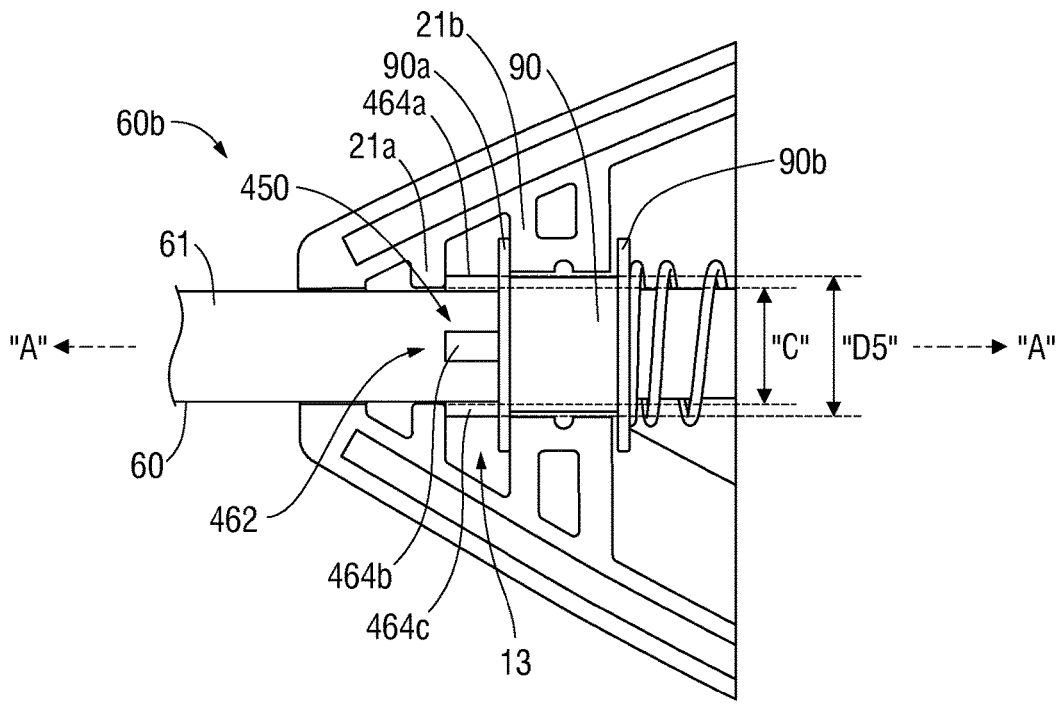
FIG. 6A is an enlarged side view of an embodiment of the stopper assembly of FIG. 2 including surface structures disposed on an outer surface of the outer shaft member.
Figure 6B:
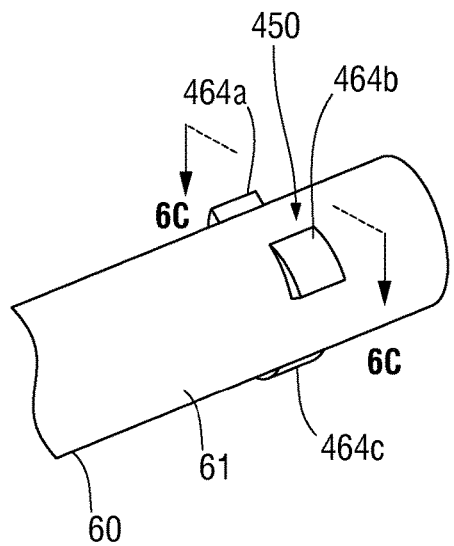
FIG. 6B is a perspective view of a portion of the outer shaft member of FIG. 6A showing the surface structures disposed on the outer surface thereof.
Figure 6C:
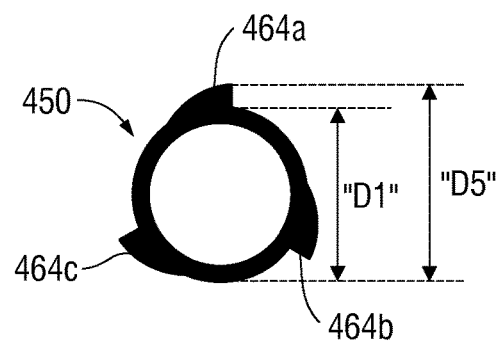
FIG. 6C is a cross-sectional view of the outer shaft member of FIG. 6B taken along section line 6C-6C of FIG. 6B.

Referring now to FIGS. 6A-6C, another embodiment of a stopper assembly 462 having a protruded portion 450 that includes a plurality of lances, for example lances 464a, 464b, and 464c, extending from the outer surface 61 of the proximal portion 60b of outer shaft member 60. In constructing outer shaft member 60 to include lances (e.g., lances 464a, 464b, 464c) as shown in FIGS. 6A-6C, stamping, punching, or other suitable processes may be employed to initially generate a flat blank of material (e.g., sheet metal) that includes a suitable profile. Thereafter, openings may be formed through the flat blank of material by any suitable equipment (e.g., metal-working equipment) and the flat blank of material pulled by a tool at the openings or pushed outward by a suitable expansion tool at the openings to create outward extending lances.

As shown in FIG. 6C, lances 464a-c effectively increase the diameter "D1" of outer shaft member 60 at the protruded portion 450 to diameter "D5". The protruded portion 450 of outer shaft member 60 is disposed within and is free to rotate within cavity 13 upon rotation of elongated member 16 about longitudinal axis "A-A". Since the diameter of the annular clearance "C" is less than the diameter "D5" of protruded portion 450, outer shaft member 60 is prevented from distal longitudinal movement along longitudinal axis "A-A" by engagement of the protruded portion 450 with distal wall 21a. Outer shaft member 60 is prevented from proximal longitudinal movement along longitudinal axis "A-A" by engagement with distal surface 90a of spindle 90.

Spindle 90, in turn, is prevented from proximal longitudinal translation along longitudinal axis "A-A" by proximal wall 21b.

Figure 7A:
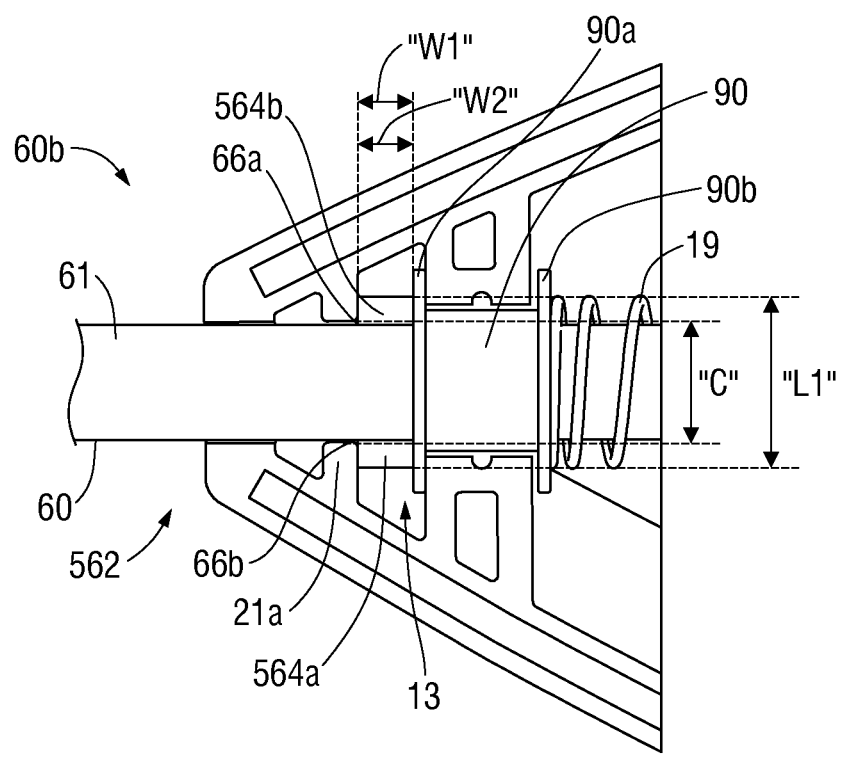
FIG. 7A is an enlarged side view of an embodiment of the stopper assembly of FIG. 2 including a key member inserted into a key slot defined through the outer shaft member.
Figure 7B:
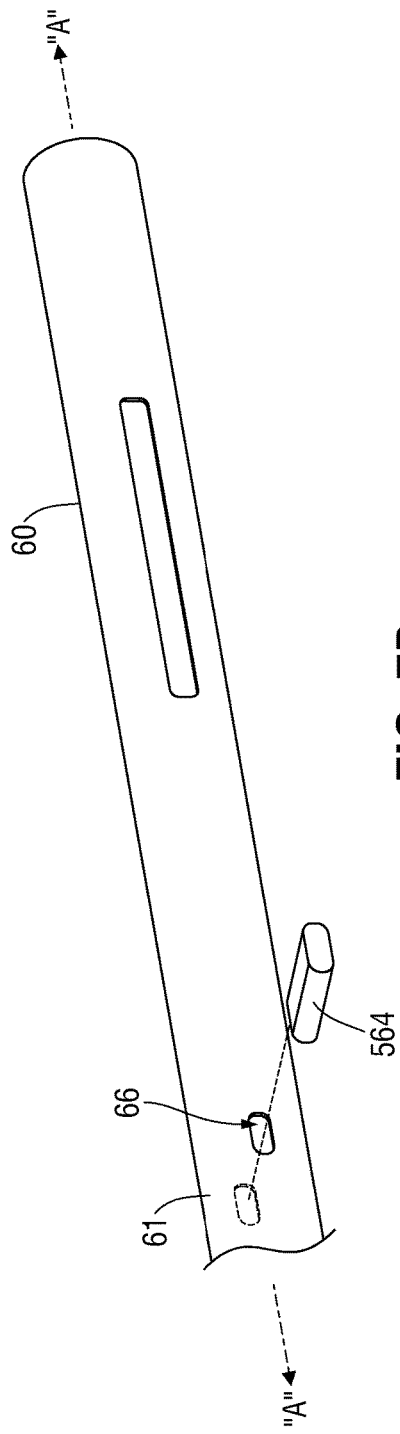
FIG. 7B is a perspective view of the outer shaft member of FIG. 7A with the key member separated from the key slot.
Figure 7C:
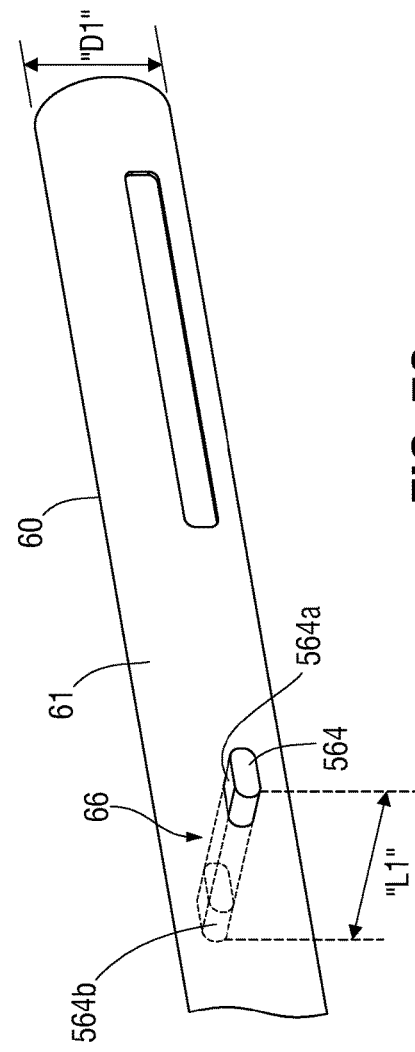
FIG. 7C is a perspective view of a portion of the outer shaft member of FIG. 7A showing the key member inserted into the key slot.

Referring now to FIGS. 7A-C, another embodiment of a stopper assembly 562 is shown and includes a key slot 66 extending through outer shaft member 60 and configured to receive a key member 564 therein in a friction fit manner. Key member 564 includes a length "L1" that is greater than the diameter "D1" of outer shaft member 60. As such, when key member 564 is inserted into key slot 66, as shown in FIG. 7C, end portions 564a, 564b of key member 564 protrude from opposite sides of outer shaft member 60. Referring to FIG. 7A, key member 564 is disposed within and free to rotate within cavity 13 upon rotation of elongated member 16 about longitudinal axis "A-A." Since key member 564 is fixedly coupled to outer shaft member 60 and the length "L1" is greater than the diameter of the annular clearance "C," distal longitudinal movement of outer shaft member 60 along longitudinal axis "A-A" is prevented due to engagement of the protruding end portions 564a, 564b of key member 564 with distal wall 21a. Similarly, due to engagement of the end portions 564a, 564b of key member 564 with the distal surface 90a of spindle 90, proximal longitudinal movement of outer shaft member 60 along longitudinal axis "A-A" is prevented. Spindle 90, in turn, is prevented from proximal longitudinal movement along longitudinal axis "A-A" by proximal wall 21b. As would be understood by those of skill in the art, internal components of elongated member 16 (e.g., knife 70) may be configured with a suitable feature (e.g., slot, recess, aperture) to accommodate key member 564 therethrough such that key member 564 does not impede longitudinal motion of these internal components along longitudinal axis "A-A".

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

The various embodiments disclosed herein may also be configured to work with robotic surgical systems and what is commonly referred to as "Telesurgery." Such systems employ various robotic elements to assist the surgeon in the operating room and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
   a housing including a cavity defined between a distal wall and a proximal wall, each of the proximal and distal walls defining an annular clearance therethrough;
   an elongated member extending distally from the housing and defining a longitudinal axis, the elongated member configured to rotate about the longitudinal axis and including an outer shaft member having a proximal portion extending through the annular clearance of each of the proximal and distal walls;
   an end effector assembly coupled to a distal portion of the elongated member, the end effector assembly including a pair of opposing jaw members moveable relative to each other to grasp tissue therebetween, at least one of the jaw members adapted to connect to an electrosurgical energy source for conducting electrosurgical energy through the grasped tissue;
   a spindle disposed on the proximal portion of the outer shaft member and disposed within the annular clearance defined through the proximal wall, the spindle including a distal portion disposed within the cavity distal to the annular clearance defined by the proximal wall and a proximal portion disposed proximal to the annular clearance defined by the proximal wall; and
   a stopper assembly disposed on the proximal portion of the outer shaft member and extending radially outward from an outer surface of the outer shaft member, the stopper assembly rotatable within the cavity upon rotation of the elongated member about the longitudinal axis and configured to engage at least one of the distal wall of the cavity or the distal portion of the spindle to prevent longitudinal movement of the outer shaft member along the longitudinal axis, the stopper assembly including:

an annular member disposed around the proximal portion of the outer shaft member and defining a pair of opposing slots aligned with a corresponding pair of opposing grooves formed in the outer surface of the outer shaft member; and a genrally u-shaped clip member having a first end portion and an opposing second end portion forming a pair of free ends extending through a respective one of the pair of opposing slots and a corresponding one of the pair of opposing grooves to maintain the annular member on the proximal portion of the outer shaft member.

2. The surgical instrument according to claim 1, wherein a diameter of the proximal and distal portions of the spindle is greater than a diameter of the annular clearance defined by the proximal wall.

3. The surgical instrument according to claim 1, wherein the spindle includes an elongated body portion extending between the proximal and distal portions of the spindle, and a diameter of the proximal and distal portions of the spindle is greater than a diameter of the elongated body portion.

4. The surgical instrument according to claim 1, wherein the pair of opposing slots are disposed perpendicular to the longitudinal axis.

5. A surgical instrument, comprising:

a housing including a cavity defined therein, the cavity defined by a distal wall and a proximal wall each defining an annular clearance;

an elongated member extending distally from the housing and defining a longitudinal axis, the elongated member configured to rotate about the longitudinal axis and including an outer shaft member having a proximal portion extending through the annular clearance of each of the distal and proximal walls;

an end effector assembly coupled to a distal portion of the elongated member, the end effector assembly including a pair of opposing jaw members moveable relative to each other to grasp tissue therebetween, at least one of the jaw members adapted to connect to an electrosurgical energy source for conducting electrosurgical energy through the grasped tissue;

a spindle disposed on the proximal portion of the outer shaft and disposed within the annular clearance defined through the proximal wall, the spindle including a distal portion disposed within the cavity distal to the annular clearance defined by the proximal wall and a proximal portion disposed proximal to the annular clearance defined by the proximal wall; and a stopper assembly disposed on the proximal portion of the outer shaft member and rotatable within the cavity upon rotation of the elongated member about the longitudinal axis, the stopper assembly extending radially outward from an outer surface of the outer shaft member and having a diameter that is greater than a diameter of the annular clearance defined through the distal wall, the stopper assembly configured to engage at least one of the distal wall or the distal portion of the spindle to prevent longitudinal movement of the outer shaft member along the longitudinal axis, the stopper assembly including:

an annular member disposed around the proximal portion of the outer shaft member and defining a pair of opposing slots aligned with a corresponding pair of opposing grooves formed in the outer surface of the outer shaft member; and a generally u-shaped clip member having a first end portion and an opposing second end portion forming a pair of free ends extending through a respective one of the pair of opposing slots and a corresponding one of the pair of opposing grooves to maintain the annular member on the proximal portion of the outer shaft member.

6. The surgical instrument according to claim 5, wherein a diameter of the proximal and distal portions of the spindle is greater than a diameter of the annular clearance defined by the proximal wall.

7. The surgical instrument according to claim 5, wherein the spindle includes an elongated body portion extending between the proximal and distal portions of the spindle, and a diameter of the proximal and distal portions of the spindle is greater than a diameter of the elongated body portion.

8. The surgical instrument according to claim 5, wherein the pair of opposing slots are disposed perpendicular to the longitudinal axis.

* * * * *